United States Patent [19]

Obara et al.

[11] Patent Number: 5,086,077
[45] Date of Patent: Feb. 4, 1992

[54] ENDERMIC MEDICAMENT WITH A GEL BASE

[75] Inventors: Sakae Obara; Hiroaki Muto; Sumiko Mizuno; Tohru Chiba, all of Niigata; Izumi Saitoh, Hyogo; Kaori Ikeda, Osaka, all of Japan

[73] Assignee: Shin-Etsu Chemical Co., Ltd., Tokyo, Japan

[21] Appl. No.: 604,921

[22] Filed: Oct. 29, 1990

[30] Foreign Application Priority Data

Nov. 7, 1989 [JP] Japan .................................. 1-289241

[51] Int. Cl.$^5$ .............................................. A61K 47/00
[52] U.S. Cl. .................................... 514/781; 514/786; 514/944; 514/946; 514/947
[58] Field of Search ............... 514/946, 947, 786, 781, 514/944

[56] References Cited

U.S. PATENT DOCUMENTS 4,543,258 9/1985 Urata et al. ........................ 514/772
4,832,943 5/1989 Grollier et al. ...................... 424/59

OTHER PUBLICATIONS

Technical Publication, Shin-Etsu Chemical Co., Ltd., Tokyo, "Metolose", pp. 1-17 (1977).
Chemical Abstracts 101:210861m (1984).

Primary Examiner—Leonard Schenkman
Attorney, Agent, or Firm—McAulay Fisher Nissen Goldberg & Kiel

[57] ABSTRACT

A novel endermic medicament having a consistency of a gel is proposed which is formulated, as a gel base, with non-ionic water-soluble cellulose ether, e.g., methyl cellulose and hydroxypropyl methyl cellulose, modified with a modification agent containing, in the molecule, an alkyl group having 6 to 26 carbon atoms and a functional group having reactivity with the hydroxyl group in the cellulose ether, e.g., stearyl glycidyl ether, decyl glycidyl ether and cetyl epoxide. The endermic medicament formulated with the modified cellulose ether is stable by virtue of the very little interaction between the active ingredients and the gel base and also can exhibit high percutaneous absorptivity of the active ingredients through the human skin.

7 Claims, No Drawings

ENDERMIC MEDICAMENT WITH A GEL BASE

BACKGROUND OF THE INVENTION

The present invention relates to an endermic medicament, i.e. a medicament for external application, with a gel base or carrier which is stable and has little interaction with the therapeutically effective ingredients contained in the medicament.

Several types of base materials for endermic medicaments are known including those for oil-base ointments, those for emulsions and those for water-soluble medicaments. As a trend in recent years, water-soluble medicaments having a gel-like consistency are highlighted by virtue of the high transparency to give a feeling of cleanness to the patients, good spreadability on the human skin, excellent percutaneous absorptivity of the therapeutically effective ingredients contained therein, easiness of removal by washing with water and other features. Several types of the gel base for such a water-soluble medicaments are already known and available on the market including carboxyvinyl polymers exhibiting excellent effects of thickening and gelation.

The above mentioned carboxyvinyl polymer is indeed an excellent gel base having high transparency to formulate an endermic medicament capable of giving satisfactory feeling of use to the patients. The polymer, however, has several problems caused by the fact that the polymer is basically a polymeric electrolyte.

The first problem in the polymer of this type is the possible interaction thereof with the therapeutically effective ingredients contained in the medicament due to the presence of the carboxyl groups in the polymer. When a gelled medicament with a basic compound as the effective ingredient is prepared with a carboxyvinyl polymer as the gel base, for example, a salt is sometimes formed between the effective ingredient and the polymeric base resulting in eventual coloration or formation of precipitates and decrease in the releasability of the effective ingredient for percutaneous absorption. On the other hand, furthermore, the gel medicament can be highly thickened only by the combined use of a basic compound for neutralization while some of basic compounds may have reactivity with the effective ingredient to cause coloration or precipitation. When the effective ingredient is ionic in the form of a salt, in addition, extensive and time-consuming investigations must be undertaken for each of the effective ingredients on the types and amounts of the basic compound for neutralization in order to obtain optimum consistency of the particular gel medicament sometimes leading to a conclusion that the amount of the basic compound for neutralization must be very large. Such a large amount of a basic compound of course has a detrimental effect against the healthy condition of the human skin to which the gel medicament is applied. Thus, carboxyvinyl polymers are under strict limitations as a gel base of endermic medicaments in respect of the formulation of the effective ingredients.

SUMMARY OF THE INVENTION

The present invention accordingly has an object to provide an endermic medicament having a consistency of a gel capable of giving an excellent feeling of use to the patients by being formulated with a novel and unique gel base which is stable exhibiting little interaction with the therapeutically effective ingredients contained in the medicament and capable of imparting a gel-like consistency to the medicament even without use of any basic compound for neutralization.

Thus, the endermic medicament having a consistency of a gel provided by the present invention comprises, as a blend:

(a) a non-ionic water-soluble cellulose ether modified with a modification agent containing, in the molecule, an alkyl group having 6 to 26 carbon atoms and a functional group having reactivity with the hydroxyl group in the cellulose ether as a base; and (b) a therapeutically active ingredient.

DETAILED DESCRIPTION OF THE PREFERRED EMBODIMENTS

As is described above, the most characteristic feature of the invention consists in the use of a unique cellulose derivative as the base of the medicament. This cellulose derivative, which has never been used as a medicament base, is stable and capable of giving very pleasant feeling of use to the patients treated with the medicament and has little reactivity with almost all kinds of therapeutically active chemical compounds.

The above defined cellulose derivative as the component (a) in the inventive medicament is prepared from a non-ionic water-soluble cellulose ether including, for example, alkyl celluloses, hydroxyalkyl celluloses and hydroxyalkyl alkyl celluloses such as methyl cellulose, hydroxyethyl cellulose, hydroxypropyl cellulose, hydroxyethyl methyl cellulose, hydroxypropyl methyl cellulose, hydroxyethyl ethyl cellulose and the like. The molecular weight of these cellulose ethers as the starting material is not particularly limitative. Usually, it is preferable for easy handling that the cellulose ether has an average molecular weight which is represented by the viscosity of a 2% by weight aqueous solution thereof in the range from 5 to 1,000.000 centipoise or, more preferably, from 200 to 300,000 centipoise at 20° C. When the molecular weight of the starting cellulose ether is too low, the cellulose derivative obtained from such a starting cellulose ether cannot impart a sufficiently high consistency to the medicament in a moderately controlled amount of addition. When the molecular weight of the starting cellulose ether is too high, on the other hand, such a cellulose ether is less reactive with the modification agent to give the modified cellulose ether suitable as the component (a).

The modification agent to be reacted with the above mentioned starting cellulose ether is a compound containing an alkyl group having from 6 to 26 carbon atoms and a functional group reactive with the hydroxyl group in the cellulose ether. When the starting cellulose ether is reacted with the modification agent, therefore, the cellulose ether is further substituted with pendant groups containing an alkyl group having 6 to 26 carbon atoms.

Various kinds of modification agents can meet the purpose including acid chlorides, isocyanates and epoxides having the above defined long-chain alkyl group in the molecule. Particular examples thereof include stearyl chloride, cetyl chloride, stearyl isocyanate, lauryl isocyanate, stearyl epoxide, cetyl epoxide, tetracosyl epoxide, hexacosyl epoxide, stearyl glycidyl ether, decyl glycidyl ether, hexyl glycidyl ether and the like though not particularly limitative thereto. These modification agents are reactive with the hydroxyl group in the cellulose ether so that alkyl groups having 6 to 26 carbon atoms are introduced into the cellulose ether substituting for the hydroxyl groups by the modification reaction which can be performed according to a known procedure.

The number of the substituent groups introduced by the above mentioned modification reaction, referred to as the modifier groups hereinafter, is selected depending on the solubility behavior thereof and the desired thickening effect exhibited when the modified cellulose ether is dissolved in the solvent used as the diluent of the gel medicament. Usually, the number of the modifier groups is in the range from about 0.01 to about 0.1 per glucose unit of the cellulose ether. As a general guide principle, the number should better be relatively small when the solvent is water and relatively large when the solvent is a mixture of water and alcohol.

The gel base of the inventive endermic medicament is prepared by dissolving the above obtained modified cellulose ether in a suitable solvent. The concentration of the cellulose derivative here is usually in the range from 0.1 to 20% by weight or, preferably, from 0.5 to 5% by weight depending on the type of the medicament. When the concentration thereof is too low, no sufficiently high consistency of the gel base can be obtained as a matter of course. When the concentration thereof is too large, on the other hand, the consistency of the medicament would be too high to be smoothly applied to and spread over the human skin so that no good feeling of use can be given to the patients forming a crusty layer after evaporation of the solvent.

The solvent to dissolve the modified cellulose ether can be water or a mixture of water with a lower alcohol and/or a polyhydric alcohol miscible with water. The lower alcohol is exemplified by ethyl alcohol, n-propyl alcohol, isopropyl alcohol and the like and the polyhydric alcohol is exemplified by glycerin, propylene glycol, polyethylene glycol and the like. Besides the solvents, the inventive endermic medicament can contain various kinds of pharmacologically permissible known adjuvants according to need including absorption aids such as isopropyl myristate, diisopropyl adipate, benzyl alcohol and the like, antiseptics, perfumes and so on.

The therapeutically effective chemical compound compounded with the above described gel base to form the inventive endermic medicament can be any of substantially almost all kinds of pharmacological compounds including antibiotics, chemotherapeutic agents, vitamins, local anaesthetics, antihistamines, astringents, sulfas, antifungals, blood-circulation promotors, adrenocortical hormones and the like depending on the therapeutic purpose of the medicament.

To summarize, the endermic medicament of the invention gives very pleasant and comfortable feeling of use to the patients and is free from limitations in the types of the therapeutically active chemicals by virtue of the inertness of the gel base as a nonionic water-soluble polymer different from conventional carboxyvinyl polymers with no risk of interaction to give versatility to the formulation of the medicament without causing problems in respect of stability. Conventional water-soluble cellulose ethers can of course be used as a gel base of a water-soluble endermic medicament although the desired thickening effect can be obtained by using a much larger amount thereof than the modified cellulose ether in the inventive medicament. Accordingly, the endermic medicaments prepared by using a conventional cellulose ether are not always quite satisfactory in respect of the feeling of stickiness or adhesiveness given to the patients treated therewith. On the contrary, the modified cellulose ether used in the inventive medicament can give a high thickening effect even when the amount thereof is greatly decreased as compared with conventional cellulose ethers and the gel medicament obtained by using the modified cellulose ether exhibits thixotropy contributing to the improvement of the feeling of use.

In the following, the endermic medicament of the invention is described in more detail by way of examples although the scope of the invention is never limited thereby in any way. The description of the inventive medicament is preceded by the description of the synthetic procedures for the preparation of the modified cellulose ethers. The term of "parts" appearing in the following description refers to "parts by weight" in each occurrence.

Synthetic Preparation 1

Into 400 g of tert-butyl alcohol were dispersed 40 g of a hydroxypropyl methyl cellulose having a molecular weight corresponding to a viscosity of 4200 centipoise of a 2% by weight aqueous solution thereof at 20° C. (Metolose 60SH-4000, a product by Shin-Etsu Chemical Co.) and the dispersion was further admixed with 35 g of a 6% aqueous solution of sodium hydroxide and agitated for 2 hours at room temperature under an atmosphere of nitrogen. Further, 130 g of stearyl glycidyl ether (Epiol SK, a product by Nippon Oils and Fats Co.) were added to the reaction mixture which was agitated for additional 4 hours at 50° C. After completion of the reaction, the reaction mixture was neutralized by adding acetic acid and cooled to room temperature followed by recovery of the solid material by filtration. The solid material thus obtained was washed with about 10 times by volume of hexane and acetone each twice and then washed with 100 times by volume of hot water at 95° C. followed by drying to give a modified cellulose ether.

The modified cellulose ether obtained in the above described manner gave a 2% by weight aqueous solution having a viscosity of 150,000 centipoise at 20° C. as measured using a Brookfield viscometer.

Synthetic Preparation 2

Into 400 g of tert-butyl alcohol were dispersed 40 g of a methyl cellulose having a molecular weight corresponding to a viscosity of 4100 centipoise of a 2% by weight aqueous solution thereof at 20° C. (Metolose SM-4000, a product by Shin-Etsu Chemical Co.) and the dispersion was further admixed with 35 g of a 6% aqueous solution of sodium hydroxide and agitated for 2 hours at room temperature under an atmosphere of nitrogen. Further, 75 g of stearyl glycidyl ether (Epiol SK, a product by Nippon Oils and Fats Co.) were added to the reaction mixture which was agitated for additional 4 hours at 50° C. After completion of the reaction, the reaction mixture was neutralized by adding acetic acid and cooled to room temperature followed by recovery of the solid material by filtration. The solid material thus obtained was washed with about 10 times by volume of hexane and acetone each twice and then washed with 100 times by volume of hot water at 95° C. followed by drying to give a modified cellulose ether.

The modified cellulose ether obtained in the above described manner gave a 2% by weight aqueous solution having a viscosity of 110,000 centipoise at 20° C. as measured using a Brookfield viscometer.

Synthetic Preparation 3

Into 400 g of tert-butyl alcohol were dispersed 40 g of the same methyl cellulose as used in Synthetic Preparation 2 described above and the dispersion was further admixed with 35 g of a 6% aqueous solution of sodium hydroxide and agitated for 2 hours at room temperature under an atmosphere of nitrogen. Further, 75 g of decyl glycidyl ether (Epiol L-41, a product by Nippon Oils and Fats Co.) were added to the reaction mixture which was agitated for additional 4 hours at 50° C. After completion of the reaction, the reaction mixture was neutralized by adding acetic acid, cooled to room temperature and admixed with 800 g of hexane followed by recovery of the solid material by filtration. The solid material thus obtained was washed with about 10 times by volume of hexane and acetone each twice and then washed with 100 times by volume of hot water at 95° C. followed by drying to give a modified cellulose ether.

The modified cellulose ether obtained in the above described manner gave a 2% by weight aqueous solution having a viscosity of 120,000 centipoise at 20° C. as measured using a Brookfield viscometer.

Synthetic Preparation 4

Into 400 g of tert-butyl alcohol were dispersed 40 g of a hydroxyethyl methyl cellulose having a molecular weight corresponding to a viscosity of 3900 centipoise of a 2% by weight aqueous solution thereof at 20° C. (SEB-04T, a product by Shin-Etsu Chemical Co.) and the dispersion was further admixed with 35 g of a 6% aqueous solution of sodium hydroxide and agitated for 2 hours at room temperature under an atmosphere of nitrogen. Further, 75 g of cetyl epoxide were added to the reaction mixture which was agitated for additional 4 hours at 50° C. After completion of the reaction, the reaction mixture was neutralized by adding acetic acid, cooled to room temperature and admixed with 800 g of hexane followed by recovery of the solid material by filtration. The solid material thus obtained was washed with about 10 times by volume of hexane and acetone each twice and then washed with 100 times by volume of hot water at 95° C. followed by drying to give a modified cellulose ether.

The modified cellulose ether obtained in the above described manner gave a 2% by weight aqueous solution having a viscosity of 110,000 centipoise at 20° C. as measured using a Brookfield viscometer.

EXAMPLE 1

Four gel bases for endermic medicaments were prepared each by dissolving 1.5 parts of one of the modified cellulose ethers obtained in the above described Synthetic Preparations 1 to 4 in a mixture of 82.5 parts of water and 16.0 parts of isopropyl alcohol. Each of the gel bases had adequate consistency suitable for application to and spreading over human skin and did not give unpleasant feeling when it was applied to and spread over the skin of testing panel members.

EXAMPLE 2

A gel medicament for external application was prepared from 1.0 part of tetracycline hydrochloride, 1.5 parts of the modified cellulose ether obtained in Synthetic Preparation 1, 81.5 parts of water and 16.0 parts of isopropyl alcohol.

For comparison, another gel medicament for external application was prepared in the same formulation as above excepting replacement of 1.5 parts of the modified cellulose ether with a combination of 0.75 part of a carboxyvinyl polymer (Carbopol 934, a product by Goodrich Co.) and 0.75 part of triethanolamine.

These gel medicaments were kept stored at room temperature to find that the first medicament according to the invention showed absolutely no changes in appearance even after 1 month of storage while formation of white precipitates was noted in the second medicament prepared for comparative purpose before long after preparation.

EXAMPLE 3

A gel medicament for external application was prepared in the same formulation as in Example 2 excepting replacement of 1.0 part of the tetracycline hydrochloride with the same amount of kanamycin sulfate and the modified cellulose ether obtained in Synthetic Preparation 1 with the same amount of the modified cellulose ether obtained in Synthetic Preparation 2.

For comparison, another gel medicament for external application was prepared in the same formulation as above excepting replacement of 1.5 parts of the modified cellulose ether with a combination of 0.75 part of a carboxyvinyl polymer (Carbopol 934, a product by Goodrich Co.) and 0.75 part of triethanolamine.

These gel medicaments were kept stored at room temperature to find that the first medicament according to the invention showed absolutely no changes in appearance even after 1 month of storage while formation of white precipitates was noted in the second medicament prepared for comparative purpose before long after preparation.

EXAMPLE 4

Five gel medicaments for external application were prepared each from 0.1 part of gentamycin sulfate, 2.0 parts of the modified cellulose ether obtained in Synthetic Preparation 1, 0.014 part of triisopropanolamine, 77.82 parts of water and 16.0 parts of an organic solvent which was one of five different solvents including ethyl alcohol, isopropyl alcohol, glycerin, polyethylene glycol 400 and propylene glycol.

For comparison, five more gel medicaments for external application were prepared each in the same formulation as above excepting replacement of the modified cellulose ether with the same amount of the same carboxyvinyl polymer as used in Example 2 for comparative purpose, increase of the amount of the triisopropanolamine to 1.4 parts and decrease of the amount of water to 76.43 parts.

These ten gel medicaments prepared according to the invention and for comparative purpose were each subjected to the in vitro releasing test according to the procedure described below.

Thus, a Franz-type permeation cell having a receptor cell of 30 ml capacity and an area for permeation of 10 $cm^2$ was used and 0.5 g of the gel medicament was applied to and evenly spread over the donor-side surface of the partitioning membrane which was a membrane filter having a pore size of 0.45 $\mu m$ made from a mixed cellulose ether (a product by Millipore Co.). The amount of the genetamycin sulfate released into the receptor cell was quantitatively determined by the fluorescent post-column high-performance liquid chromatography after lapse of a length of time. The results obtained with the gel medicaments prepared according to the invention are shown in Table 1 below in $\mu g$.

Absolutely no release could be found of the gentamycin sulfate when the gel medicament applied to the membrane surface was prepared using the carboxyvinyl polymer as the gel base while the releasability of the active ingredient was good in each of the inventive medicaments although the rate of release was dependent on the kind of the solvent to some extent as is shown in the table.

EXAMPLE 5

A gel medicament for external application was prepared from 1.0 part of croconazole hydrochloride, 2.0 parts of the modified cellulose ether obtained in Synthetic Preparation 1, 0.6 part of triisopropanolamine, 48.5 parts of water, 31.5 parts of propylene glycol and 16.4 parts of isopropyl alcohol.

An in vivo percutaneous absorption test of the thus prepared endermic medicament was undertaken using rats as the test animals in the procedure described below. As a control, the same percutaneous absorption test was undetaken with a commercial product of an endermic medicament having a similar consistency and containing croconazole hydrochloride in the same concentration as above (Pilzcin Gel, a product by Shionogi & Co.).

TABLE 1

| Solvent | Time, hours | Amount released, μg |
|---|---|---|
| Ethyl alcohol | 1 | 312 |
| | 2 | 370 |
| | 6 | 434 |
| Isopropyl alcohol | 1 | 357 |
| | 2 | 458 |
| | 4 | 492 |
| Glycerin | 0.5 | 156 |
| | 1 | 253 |
| | 2 | 321 |
| Polyethylene glycol 400 | 0.5 | 260 |
| | 1 | 351 |
| | 2 | 404 |
| Propylene glycol | 0.5 | 222 |
| | 1 | 285 |
| | 2 | 367 |

Thus, a 0.3 g portion of the gel medicament was applied to and spread over the shaved abdominal skin of a male rat of the Wister strain and the medicament was recovered after 4 hours by washing with ethyl alcohol. Separately, the abdominal skin of the rat after removal of the gel medicament was taken by resection. The amounts of the croconazole hydrochloride in the ethyl alcohol washing and in the resected abdominal skin were determined by the high-performance liquid chromatography to give the results shown in Table 2 below.

TABLE 2

| | Recovery, %, in washing | Amount, μg, retained in the skin |
|---|---|---|
| Inventive medicament | 92.5 | 22.6 |
| Commercial medicament | 98.3 | 8.3 |

The results shown in Table 2 clearly indicate that the percutaneous absorptivity of the therapeutically effective ingredient is much higher in the inventive endermic medicament than in the commercial medicament of the similar type.

What is claimed is:

1. An endermic medicament having a consistency of a gel which comprises, as a blend:
   (a) a non-ionic water-soluble cellulose ether modified by reaction with a modification agent containing, in the molecule, an alkyl group having 6 to 26 carbon atoms and a functional group having reactivity with the hydroxyl group in the cellulose ether as a base; and
   (b) a therapeutic effective amount of a therapeutically active ingredient.

2. The endermic medicament as claimed in claim 1 in which the non-ionic water-soluble cellulose ether to be modified with the modification agent is selected from the group consisting of alkyl celluloses, hydroxyalkyl celluloses and hydroxyalkyl alkyl celluloses.

3. The endermic medicament as claimed in claim 1 in which the modification agent is selected from the group consisting of stearyl chloride, cetyl chloride, stearyl isocyanate, lauryl isocyanate, stearyl epoxide, cetyl epoxide, tetracosyl epoxide, hexacosyl epoxide, stearyl glycidyl ether, decyl glycidyl ether and hexyl glycidyl ether.

4. The endermic medicament as claimed in claim 1 in which the non-ionic water-soluble cellulose ether is modified with the modification agent in such a degree that an average of from 0.01 to 0.1 of the hydroxyl groups per glucose unit of the cellulose ether are substituted by the modification agent.

5. The endermic medicament as claimed in claim 1 which further comprises a solvent which dissolves the non-ionic water-soluble cellulose ether modified with the modification agent.

6. The endermic medicament as claimed in claim 5 in which the solvent is water or a mixture of water and an organic solvent selected from the group consisting of water-soluble lower alcohols and water-soluble polyhydric alcohols.

7. The endermic medicament as claimed in claim 5 in which the concentration of the non-ionic water-soluble cellulose ether modified with the modification agent is in the range from 0.1 to 20% by weight.

* * * * *